(12) United States Patent
Zupkofska

(10) Patent No.: US 10,166,126 B2
(45) Date of Patent: Jan. 1, 2019

(54) INFLATABLE BALLOON STENT

(71) Applicant: BOSTON SCIENTIFIC SCIMED, INC., Maple Grove, MN (US)

(72) Inventor: Michael E. Zupkofska, Rockland, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 216 days.

(21) Appl. No.: 14/962,790

(22) Filed: Dec. 8, 2015

(65) Prior Publication Data
US 2016/0158040 A1 Jun. 9, 2016

Related U.S. Application Data

(60) Provisional application No. 62/089,013, filed on Dec. 8, 2014.

(51) Int. Cl.
| *A61F 2/06* | (2013.01) |
| *A61F 2/82* | (2013.01) |
| *A61F 2/848* | (2013.01) |
| *A61F 2/04* | (2013.01) |
| *A61F 2/844* | (2013.01) |
| *A61F 2/94* | (2013.01) |
| *A61F 2/966* | (2013.01) |
| *A61F 2/00* | (2006.01) |

(52) U.S. Cl.
CPC ............... *A61F 2/82* (2013.01); *A61F 2/844* (2013.01); *A61F 2/848* (2013.01); *A61F 2/94* (2013.01); *A61F 2/966* (2013.01); *A61F 2002/0081* (2013.01); *A61F 2002/044* (2013.01); *A61F 2230/001* (2013.01); *A61F 2250/0003* (2013.01); *A61F 2250/0039* (2013.01)

(58) Field of Classification Search
None
See application file for complete search history.

(56) References Cited

U.S. PATENT DOCUMENTS

| | | | |
|---|---|---|---|
| 5,370,691 A | 12/1994 | Samson | |
| 6,007,575 A | 12/1999 | Samuels | |
| 6,395,019 B2 | 5/2002 | Chobotov | |
| 6,729,356 B1 | 5/2004 | Baker et al. | |
| 6,776,604 B1 | 8/2004 | Chobotov et al. | |
| 7,108,715 B2 | 9/2006 | Lawrence-Brown et al. | |
| 7,468,072 B2 | 12/2008 | Morsi | |
| 7,658,762 B2 | 2/2010 | Lashinski et al. | |

(Continued)

FOREIGN PATENT DOCUMENTS

| EP | 441516 B1 | 3/1995 |
|---|---|---|
| WO | 2009086200 A1 | 7/2009 |

(Continued)

*Primary Examiner* — Thomas J Sweet
*Assistant Examiner* — Tiffany Shipmon
(74) *Attorney, Agent, or Firm* — Seager, Tufte & Wickhem, LLP

(57) ABSTRACT

An illustrative stent may comprise an elongated tubular balloon having a first end and a second end and an intermediate region disposed therebetween. The elongated tubular balloon may have an inner wall and an outer wall, the inner wall and the outer wall connected at the first end and the second end to define an enclosed inflation chamber between the inner wall and the outer wall. The stent may further include an inflation valve.

15 Claims, 8 Drawing Sheets

(56) References Cited

U.S. PATENT DOCUMENTS

| | | |
|---|---|---|
| 7,678,217 B2 | 3/2010 | Chobotov et al. |
| 7,766,954 B2 * | 8/2010 | Chobotov ............... A61F 2/07 623/1.13 |
| 7,803,178 B2 | 9/2010 | Whirley et al. |
| 8,216,297 B2 | 7/2012 | Kari |
| 8,226,708 B1 | 7/2012 | Murch |
| 8,377,118 B2 | 2/2013 | Lashinksi et al. |
| 9,144,486 B2 | 9/2015 | Vinluan |
| 9,179,921 B1 * | 11/2015 | Morris ............ A61B 17/12099 |
| 2005/0055082 A1 * | 3/2005 | Ben Muvhar ............ A61F 2/91 623/1.15 |
| 2006/0167538 A1 * | 7/2006 | Rucker ................. A61F 2/04 623/1.25 |
| 2009/0082857 A1 | 3/2009 | Lashkinski et al. |
| 2009/0187240 A1 | 7/2009 | Clerc et al. |
| 2010/0331958 A1 | 12/2010 | Chobotov |
| 2011/0160751 A1 | 6/2011 | Granja Filho |
| 2011/0213460 A1 | 9/2011 | Lashinski et al. |
| 2011/0218609 A1 | 9/2011 | Chobotov et al. |
| 2012/0191174 A1 | 7/2012 | Vinluan et al. |
| 2013/0018452 A1 | 1/2013 | Weitzner et al. |
| 2013/0090715 A1 | 4/2013 | Chobotov |
| 2013/0268044 A1 | 10/2013 | Parsons et al. |
| 2014/0081311 A1 | 3/2014 | Carmeli et al. |
| 2014/0121747 A1 | 5/2014 | Clerc et al. |
| 2014/0194970 A1 | 7/2014 | Chobotov |
| 2014/0243950 A1 | 8/2014 | Weiner |
| 2014/0277560 A1 | 9/2014 | Walak |
| 2014/0288637 A1 | 9/2014 | Clerc et al. |
| 2015/0157479 A1 | 6/2015 | Parsons et al. |
| 2016/0158040 A1 | 6/2016 | Zupkofska |

FOREIGN PATENT DOCUMENTS

| | | |
|---|---|---|
| WO | 2012068175 A2 | 5/2012 |
| WO | 2015138402 A1 | 9/2015 |

* cited by examiner

INFLATABLE BALLOON STENT

CROSS-REFERENCE TO RELATED APPLICATIONS

This application claims priority under 35 U.S.C. § 119 to U.S. Provisional Application Ser. No. 62/089,013, filed Dec. 8, 2014, the entirety of which is incorporated herein by reference.

TECHNICAL FIELD

The present disclosure pertains to medical devices, and methods for manufacturing medical devices. More particularly, the present disclosure pertains to an inflatable stent.

BACKGROUND

Implantable stents are devices that are placed in a body structure, such as a blood vessel or body cavity, to provide support and to maintain the structure open. These devices are manufactured by any one of a variety of different manufacturing methods and may be used according to any one of a variety of methods. Of the known medical devices, delivery system, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices. An example medical device may include a stent. The stent comprises:

an elongated tubular balloon having a first end and a second end and an intermediate region disposed therebetween, the elongated tubular balloon having an inner wall and an outer wall, the inner wall and the outer wall connected at the first end and the second end to define an enclosed inflation chamber between the inner wall and the outer wall; and an inflation valve.

Alternatively or additionally to any of the embodiments above, an inner surface of the inner wall of the elongated tubular balloon defines a lumen extending from the first end to the second end.

Alternatively or additionally to any of the embodiments above, the inflation valve comprises a one-way valve.

Alternatively or additionally to any of the embodiments above, the inflation valve comprises a break away valve.

Alternatively or additionally to any of the embodiments above, the inflation valve is disposed adjacent to the first end of the elongated tubular balloon.

Alternatively or additionally to any of the embodiments above, the inflation valve is disposed adjacent to the second end of the elongated tubular balloon.

Alternatively or additionally to any of the embodiments above, the inflation valve is disposed adjacent to the intermediate region of the elongated tubular balloon.

Alternatively or additionally to any of the embodiments above, a first end region of the elongated tubular balloon has an outer diameter larger than an outer diameter of the intermediate region.

Alternatively or additionally to any of the embodiments above, a second end region of the elongated tubular balloon has an outer diameter larger than an outer diameter of the intermediate region.

Alternatively or additionally to any of the embodiments above, the elongated tubular balloon has a uniform outer diameter from the first end to the second end.

Alternatively or additionally to any of the embodiments above, a portion of an outer surface of the outer wall comprises a textured surface.

Alternatively or additionally to any of the embodiments above, the portion of the outer surface comprise the entire outer surface of the outer wall.

Alternatively or additionally to any of the embodiments above, the textured surface includes raised projections.

Alternatively or additionally to any of the embodiments above, the elongated tubular balloon comprises polyethylene terephthalate.

Alternatively or additionally to any of the embodiments above, the stent has at least one radiopaque marker element.

Another example stent comprises:

an elongated tubular balloon having a first end and a second end and an intermediate region disposed therebetween, the elongated tubular balloon having an inner wall and an outer wall, the inner wall and the outer wall connected at the first end and the second end to define an enclosed inflation chamber between the inner wall and the outer wall; and an inflation valve.

Alternatively or additionally to any of the embodiments above, an inner surface of the inner wall of the elongated tubular balloon defines a lumen extending from the first end to the second end.

Alternatively or additionally to any of the embodiments above, the inflation valve is disposed adjacent to one of the first or second ends of the elongated tubular balloon.

Alternatively or additionally to any of the embodiments above, the inflation valve is disposed adjacent to the intermediate region of the elongated tubular balloon.

Alternatively or additionally to any of the embodiments above, the first end has an outer diameter larger than an outer diameter of the intermediate region and the second end has an outer diameter larger than an outer diameter of the intermediate region.

Alternatively or additionally to any of the embodiments above, the inflation valve comprises a one-way valve.

Alternatively or additionally to any of the embodiments above, the inflation valve comprises a break away valve.

Alternatively or additionally to any of the embodiments above, an outer surface of the outer wall comprises a textured surface.

Alternatively or additionally to any of the embodiments above, the textured surface includes raised projections.

Alternatively or additionally to any of the embodiments above, the elongated tubular balloon comprises polyethylene terephthalate.

Alternatively or additionally to any of the embodiments above, the stent has at least one radiopaque marker element.

Another example stent comprises:

an elongated tubular balloon, the elongated tubular balloon comprising:
- a flared first end and a flared second end and an intermediate region disposed therebetween;
- an inner wall and an outer wall, the inner wall and the outer wall connected at both the first end and the second end to define an enclosed inflation chamber between the inner wall and the outer wall;

wherein an inner surface of the inner wall of the elongated tubular balloon defines a lumen extending from the first end to the second end of the elongated tubular balloon; and an inflation valve disposed adjacent to the first end of the elongated tubular balloon.

Alternatively or additionally to any of the embodiments above, the flared first end has an outer diameter larger than an outer diameter of the intermediate region.

Alternatively or additionally to any of the embodiments above, the flared second end has an outer diameter larger than an outer diameter of the intermediate region.

Alternatively or additionally to any of the embodiments above, the inflation valve comprises a one-way valve.

Alternatively or additionally to any of the embodiments above, a portion of an outer surface of the outer wall comprises a textured surface.

Alternatively or additionally to any of the embodiments above, the textured surface includes raised projections.

Alternatively or additionally to any of the embodiments above, the elongated tubular balloon comprises polyethylene terephthalate.

Alternatively or additionally to any of the embodiments above, the stent has at least one radiopaque marker element.

Another example stent comprises:

an elongated tubular balloon, the elongated tubular balloon comprising:

a flared proximal end having a first outer diameter and a flared distal end having a second outer diameter and an intermediate region having a third outer diameter smaller than both the first outer diameter and the second outer diameter disposed between the flared proximal end and the flared distal end;

an inner wall and an outer wall extending along a length of the elongated tubular balloon, the inner wall and the outer wall connected at both the proximal end and the distal end to define an enclosed inflation chamber between the inner wall and the outer wall;

wherein an inner surface of the inner wall of the elongated tubular balloon defines a through lumen extending from the proximal end to the distal end of the elongated tubular balloon; and an inflation valve disposed adjacent to the proximal end of the elongated tubular balloon.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments in connection with the accompanying drawings, in which.

Figure 1:
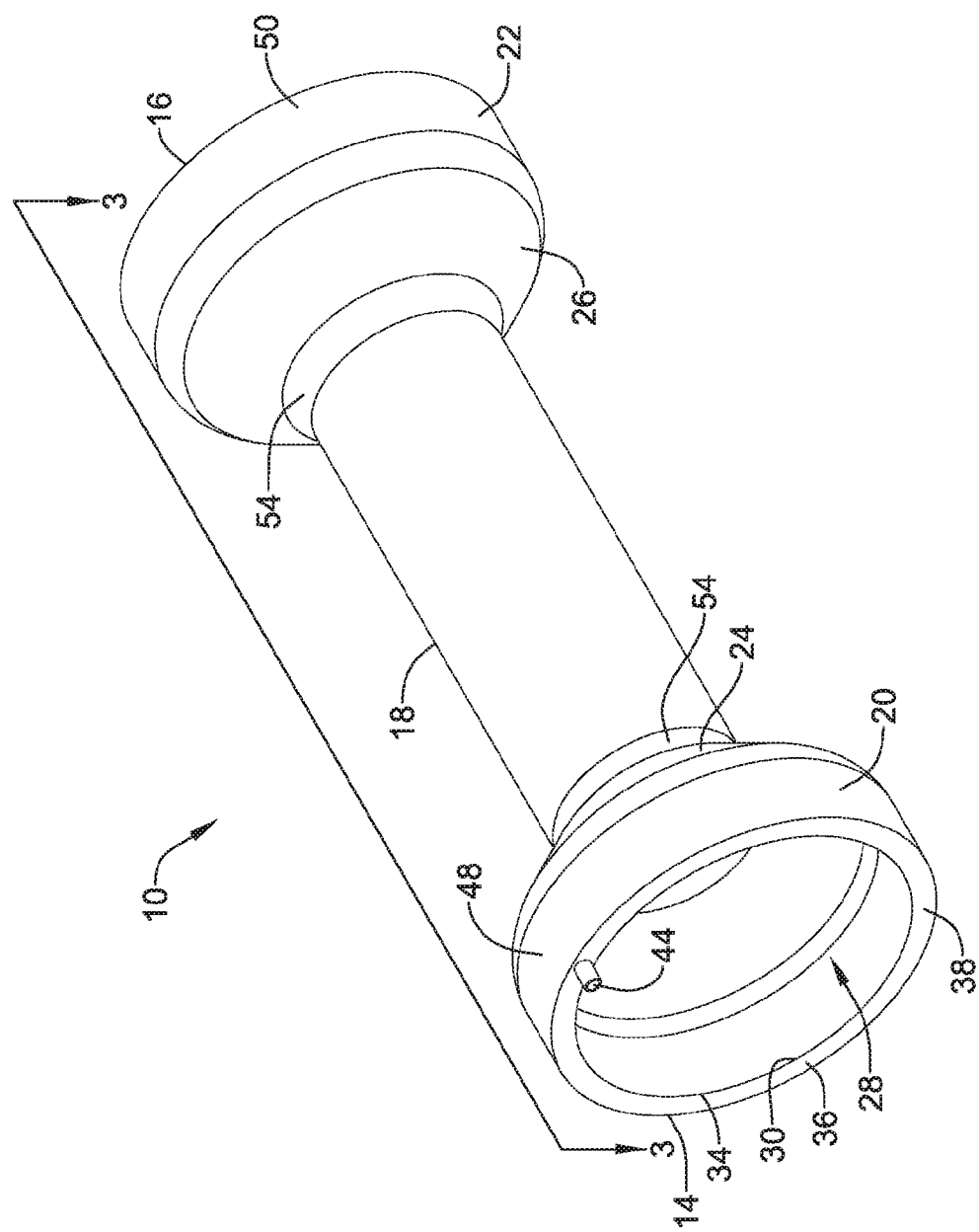
FIG. 1 is a perspective view of an illustrative inflatable stent.

While the disclosure is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

In some instances, it may be desirable to provide an endoluminal implant, or stent, that can deliver luminal patency in patients with esophageal strictures. Such stents may be used in patients experiencing dysphagia, sometime due to esophageal cancer. An esophageal stent may allow a patient to maintain nutrition via oral intake during cancer treatment or palliation periods. However, traditional wire stents may pose a problem for radiation treatments. It may be desirable to provide a stent that can deliver luminal patency while minimizing interference with radiation, or other, treatments. While the embodiments disclosed herein are discussed with reference to esophageal stents, it is contemplated that the stents described herein may be used and sized for use in other locations such as, but not limited to: bodily tissue, bodily organs, vascular lumens, nonvascular lumens and combinations thereof, such as, but not limited to, in the coronary or peripheral vasculature, trachea, bronchi, colon, small intestine, biliary tract, urinary tract, prostate, brain, stomach and the like.

Figure 2:
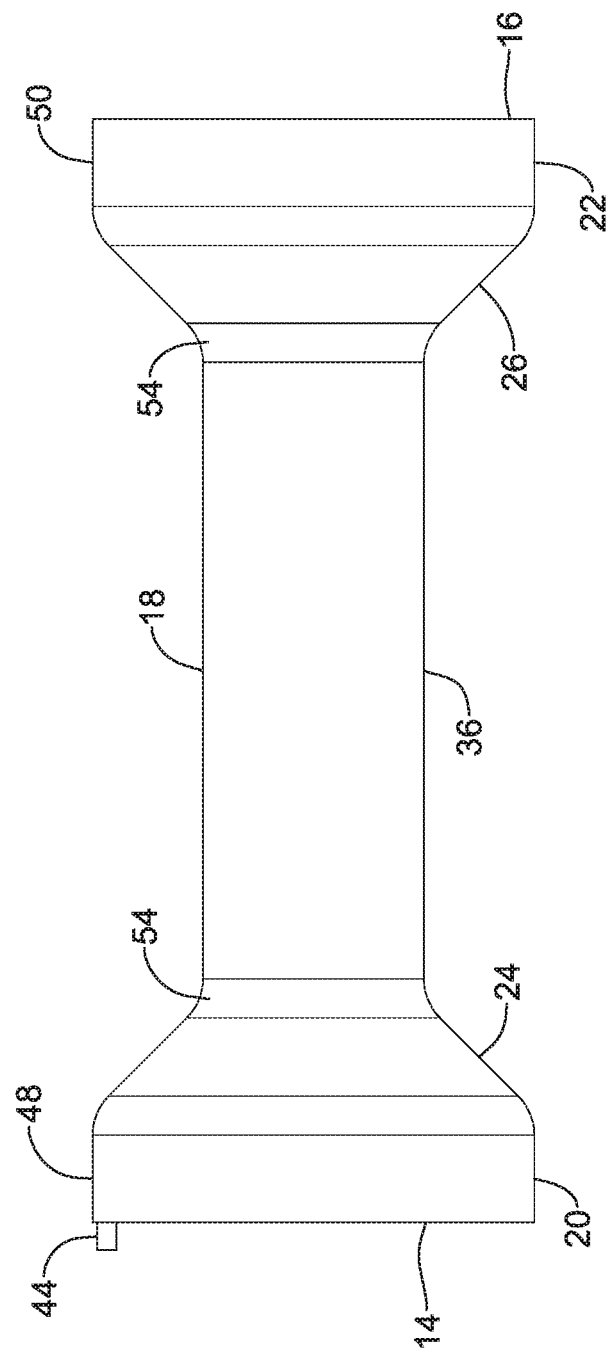
FIG. 2 is a side view of the illustrative inflatable stent of FIG. 1.

FIG. 1 illustrates a perspective view of an illustrative endoluminal implant 10, such as, but not limited to, a stent. A side view of the illustrative stent 10 of FIG. 1 is illustrated in FIG. 2. Referring to both FIGS. 1 and 2, in some instances, the stent 10 may be formed from an elongated tubular balloon having a first end 14, a second end 16, and an intermediate region 18 disposed between the first end 14 and the second end 16. The stent 10 may be expandable from a first collapsed configuration (see, for example, FIG. 4) to a second expanded configuration. The stent 10 may be structured to extend across a stricture and to apply a radially outward pressure to the stricture in a lumen to open the lumen and allow for the passage of foods, fluids, air, etc. In some instances, in the expanded configuration, the stent 10 may include a first end region 20 and a second end region 22. In some embodiments, the first end region 20 and the second end region 22 may include retention features or anti-migration flares 48, 50 positioned adjacent to the first end 14 and the second end 16 of the stent 10. The anti-migration flares 48, 50 may be configured to engage an interior portion the walls of the esophagus. In some embodiments, the retention features 48, 50 may have a larger diameter than an intermediate portion 18 of the stent 10 to prevent the stent 10 from migrating once placed in the esophagus. It is contemplated that the transition 24, 26 from the cross-sectional area of the intermediate region 18 to the retention features 48, 50 may be gradual, sloped, or occur in an abrupt step-wise manner, as desired.

In some embodiments, the first anti-migration flare 48 may have a first outer diameter and the second anti-migration flare 50 may have a second outer diameter. In some instances, the first and second outer diameters may be approximately the same, while in other instances, the first and second outer diameters may be different. In some embodiments, the stent 10 may include only one or none of the anti-migration flares 48, 50. For example, the first end region 20 may include an anti-migration flare 48 while the second end region 22 may have an outer diameter similar to the intermediate region 18. It is further contemplated that the second end region 22 may include an anti-migration flare 50 while the first end region 20 may have an outer diameter similar to an outer diameter of the intermediate region 18. These are just examples. In some embodiments, the stent 10 may have a uniform outer diameter from the first end 14 to the second end 16. In some embodiments, the outer diameter of the intermediate region 18 may be in the range of 15 to 25 millimeters. The outer diameter of the anti-migration flares 48, 50 may be in the range of 20 to 30 millimeters. These are just examples. It is contemplated that the outer diameter of the stent 10 may be varied to suit the desired application.

Figure 3:
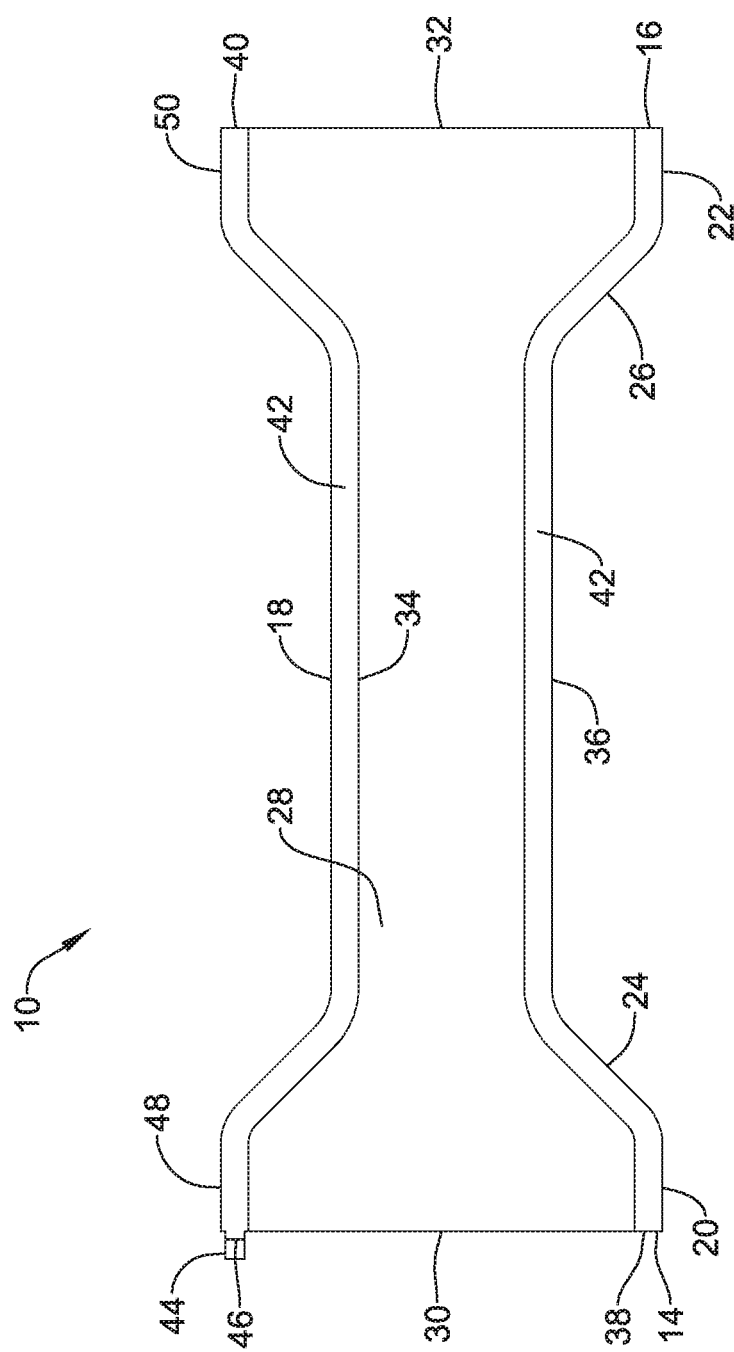
FIG. 3 is a cross-sectional view of the illustrative stent of FIG. 1 taken at line 3-3 of FIG. 1.

Referring additionally to FIG. 3, which illustrates a cross-sectional view of the illustrative stent 10 taken at line 3-3 of FIG. 1, the stent 10 may be formed from an elongated tubular inflatable balloon. While the stent 10 is described as generally tubular, it is contemplated that the stent 10 may take any cross-sectional shape desired. In some embodiments, the stent 10 may be formed from a high pressure material, such as, but not limited to, polyethylene terephthalate (PET), nylon, polyethylene (PE), polyurethane, or flexible polyvinyl chloride (PVC). In other embodiments, the stent 10 may be formed from a compliant, low pressure material, such as, but not limited to, silicone, synthetic polyisoprene, or latex. The outer surface of the stent 10 may be generally solid which may help reduce food impaction and tumor or tissue ingrowth. The stent 10 may include a lumen 28 extending from a first opening 30 adjacent the first end 14 to a second opening 32 adjacent to the second end 16 to allow for the passage of food, fluids, etc. The stent 10 may include an inner wall 34 and an outer wall 36. The inner wall 34 and the outer wall 36 may be connected by one or more side walls 38, 40 adjacent the first and second ends 14, 16 to define an enclosed inflation chamber 42 extending from the first end 14 to the second end 16. In other embodiments, the inner wall 34 and the outer wall 36 may be secured directly to one another without the use of side walls 38, 40. The inflation chamber 42 may receive an inflation fluid through an inflation port or valve 44 to expand the stent 10 from a generally collapsed delivery configuration (see, for example, FIG. 4) to an expanded or deployed configuration, as shown in FIGS. 1-3. The inflation fluid may be saline, a biocompatible liquid polymer, such as ENTERYX®, air, or other suitable inflation fluid.

While the inflation chamber 42 is shown as extending along the entire length of the stent 10, other configurations are contemplated. In some instances, inflation chamber 42 may extend along only a portion of the length of the stent 10. For example, the inflation chamber 42 extend along one or both of the first or second end regions 20, 22. In other embodiments, the inflation chamber 42 may be a plurality of longitudinal chambers extending from the first end 14 to the second end 16 separated by non-inflatable regions. In yet other embodiments, the inflation chamber 42 may be a plurality of annular rings extending about the circumference of the stent 10 separated by non-inflatable regions. In some instances, the inflation chamber 42 may be helical chamber, winding about the circumference of the stent 10 from the first end 14 to the second end 16. It is contemplated that a plurality of inflation chambers may be fluidly connected to allow a single inflation valve 44 to provide an inflation fluid to each of the chambers. However, this is not required. A plurality of inflation valves may be provided to supply each of the inflation chambers, individually or in groups, with an inflation fluid. These are just examples.

An inflation port or valve 44 may be positioned adjacent to the first end 14. However, in some instances, the inflation valve 44 may be positioned adjacent to the second end 16 or in the intermediate region 18, as desired. The inflation valve 44 may be in fluid communication with the inflation chamber 42 to provide a regulated passage for an inflation fluid to travel into the inflation chamber 42 of the stent 10. The inflation valve 44 may be any of a number of widely applied valves, applicable in surgeries and medical implants, and may be made from a biocompatible material. In some embodiments, the inflation valve 44 may be a unidirectional, or one-way, valve that provides a regulated passage for an amount of a suitable fluid into the inflation chamber 42 of the inflatable stent 10. For example, the inflation valve 44 may provide such a passage upon an application of pressure from a catheter lumen or an inflation device that is introduced into the stent 10 for the stent's inflation. Once the application of pressure is removed, a diaphragm or other sealing mechanism 46 may seal the inflation chamber 42 to maintain the stent 10 in the inflated state.

In some embodiments, the inflation valve 44 may comprise a break away port. The valve 44 may be affixed to a delivery device during delivery and inflation of the stent 10 and break away from the delivery device and/or the stent 10 once the stent 10 has been inflated to a desired pressure. While the inflation valve 44 is illustrated as extending from the first end 14 of the stent 10, it is contemplated that the inflation valve 44 may be positioned at other location along the stent 10, as desired. For example, in some instances, the inflation valve 44 may be incorporated into the inflation chamber 42 such that it does not extend beyond the first end 14. In other instances, the inflation valve 44 may be disposed adjacent the second end 16. It is further contemplated that the inflation valve 44 may be positioned with the lumen 28 of the stent 10. For example, the inflation valve 44 may be positioned adjacent to the intermediate region 18 and accessible through the lumen 28 of the stent 10. These are just examples.

The stent 10 may further include one or more radiopaque marker elements 54. The marker elements 54 may be doped with, made of, or otherwise include a radiopaque material. Radiopaque materials are understood to be materials capable of producing a relatively bright image on a fluoroscopy screen or another imaging technique during a medical procedure. The marker elements 54 may be positioned at any location along the length of the stent 10 desired. In some instances, the marker elements 54 may be positioned adjacent to one or both of the first or second end regions 20, 22 to facilitate positioning of the anti-migration flares 48, 50. This is just an example.

Figure 4:
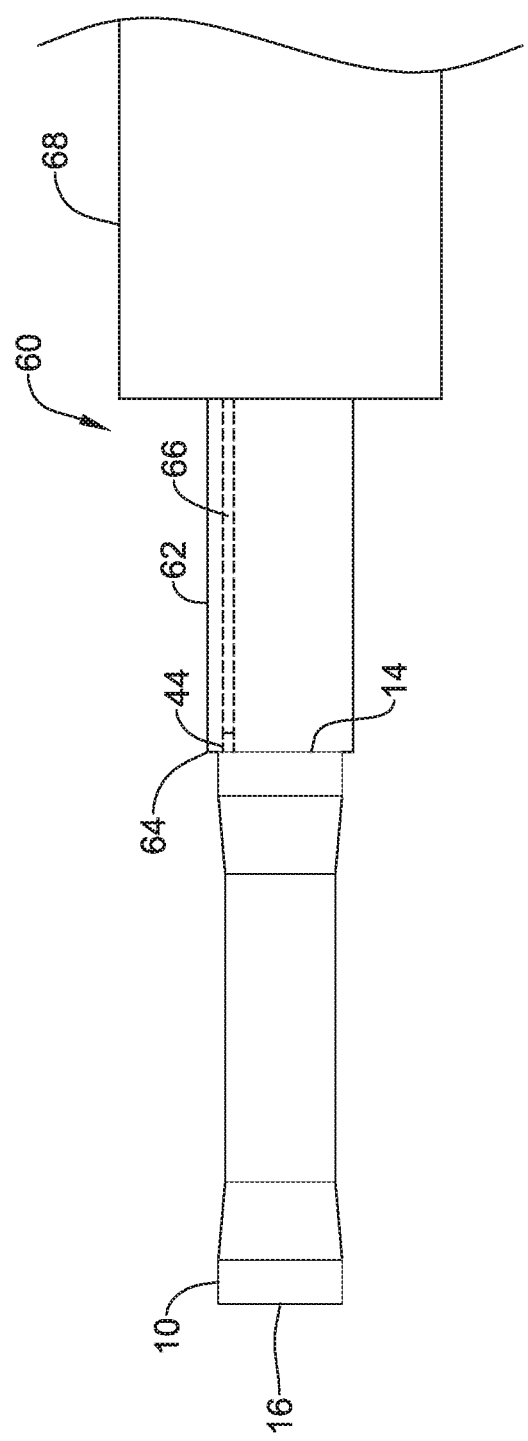
FIG. 4 a side view of a distal end region of an illustrative stent delivery system.

FIG. 4 is a side view of a distal end region of an illustrative stent delivery system 60 for delivering an inflatable stent, such as stent 10. The stent delivery system 60 may include an elongate catheter shaft 62 having a proximal end (not shown) and a distal end 64. The catheter shaft 62 may extend proximally from the distal end 64 to the proximal end which is configured to remain outside of a patient's body. Although not shown, the proximal end of the catheter shaft 62 may include a hub attached thereto for connecting other treatment devices or providing a port for facilitating other treatments. It is contemplated that the stiffness and size of the catheter shaft 62 may be modified to form a delivery system 60 for use in various locations within the body. The catheter shaft 62 may further define a lumen 66 through which an inflation fluid may be passed. While not explicitly shown, the catheter shaft 62 may include one or more additional lumens through which a guidewire (not explicitly shown) may be passed in order to advance the catheter to a predetermined position, although this is not required. The stent delivery system 60 may be configured to be advanced through a working channel of an endoscope, gastroscope or other guide means 68.

The stent 10 may be releasably coupled or secured to the catheter shaft 62 at the inflation valve 44. For example, the inflation valve 44 may be disposed within and/or secured to the inflation lumen 66. As discussed above, the inflation valve 44 may comprise a break away port. The valve 44 may be affixed to the catheter shaft 62 during delivery and inflation of the stent 10 and break away from the catheter shaft 62 and/or stent 10 once the stent 10 has been inflated to a desired pressure. In other embodiments, the stent 10, in the collapsed or uninflated state, may be wrapped around a distal portion of the catheter shaft 62. Other mechanisms for releasably securing the stent 10 to the catheter shaft 62 are contemplated.

During delivery of the stent 10, the guide means 68 may be positioned across or adjacent to the desired location of the stent 10. The catheter shaft 62, including stent 10, may be advanced through a lumen of the guide means 68. In some instances, the inflatable stent 10 may be wrapped, folded, or otherwise collapsed and/or compressed while the stent 10 is being advanced to the target location. The guide means 68 may help maintain the stent 10 in the collapsed position while the stent 10 is advanced to the target location. Once the stent 10 is near the target location, the catheter shaft 62 may be distally advanced from the guide means 68, or the guide means 68 may be proximally retracted, to advance the stent 10 from within the guide means 68. Once the stent 10 is in the desired position, an inflation fluid may be supplied through the inflation lumen 66 to the inflation valve 44 and into inflation chamber 42 to inflate or expand the stent 10. The flow of inflation fluid may continue until the stent 10 achieves a desired pressure. It is contemplated that the pressure of the inflation fluid may be sufficient to deform a sealing mechanism, such as sealing mechanism 46, within the valve 44 to allow fluid to flow into the inflation chamber 42. Once the flow of fluid is stopped, the sealing mechanism 46 may close, thus maintaining the stent 10 in the inflated or expanded state. The catheter shaft 62 and the guide means 68 may be removed from the body while leaving the stent 10 at the desired location in the body. It is contemplated that the radial force of the stent 10 and/or anti-migration flares 48, 50 may be sufficient to maintain the stent in the desired location. In some embodiments, the stent 10 may be sutured to the esophagus to further secure the stent 10 in the desired location. The stent 10 may include additional material and/or structure separate from the inflation chamber 42 to allow the sutures to be secured to the stent 10 without puncturing the inflation chamber 42.

It is contemplated that the stent 10 may be removable after a desired time frame, such as, in the range of: one year, less than one year, less than 9 months, less than 6 months, or less than 3 months. In some instances, the application of a mechanical force may allow the sealing mechanism 46 of the valve 44 to deform and release some of the inflation fluid. It is contemplated that the inflation fluid may be removed from the body through aspiration or other mechanism, or allowed to be absorbed into or pass through the body. The release of some of the inflation fluid may reduce the pressure of the inflatable stent 10 thus allowing for easier removal from the body lumen. It is contemplated that the stent 10 may be removed from the body using devices, such as, but not limited to rat-tooth jaws, forceps, or other grasping or retrieval mechanisms.

Figure 5:
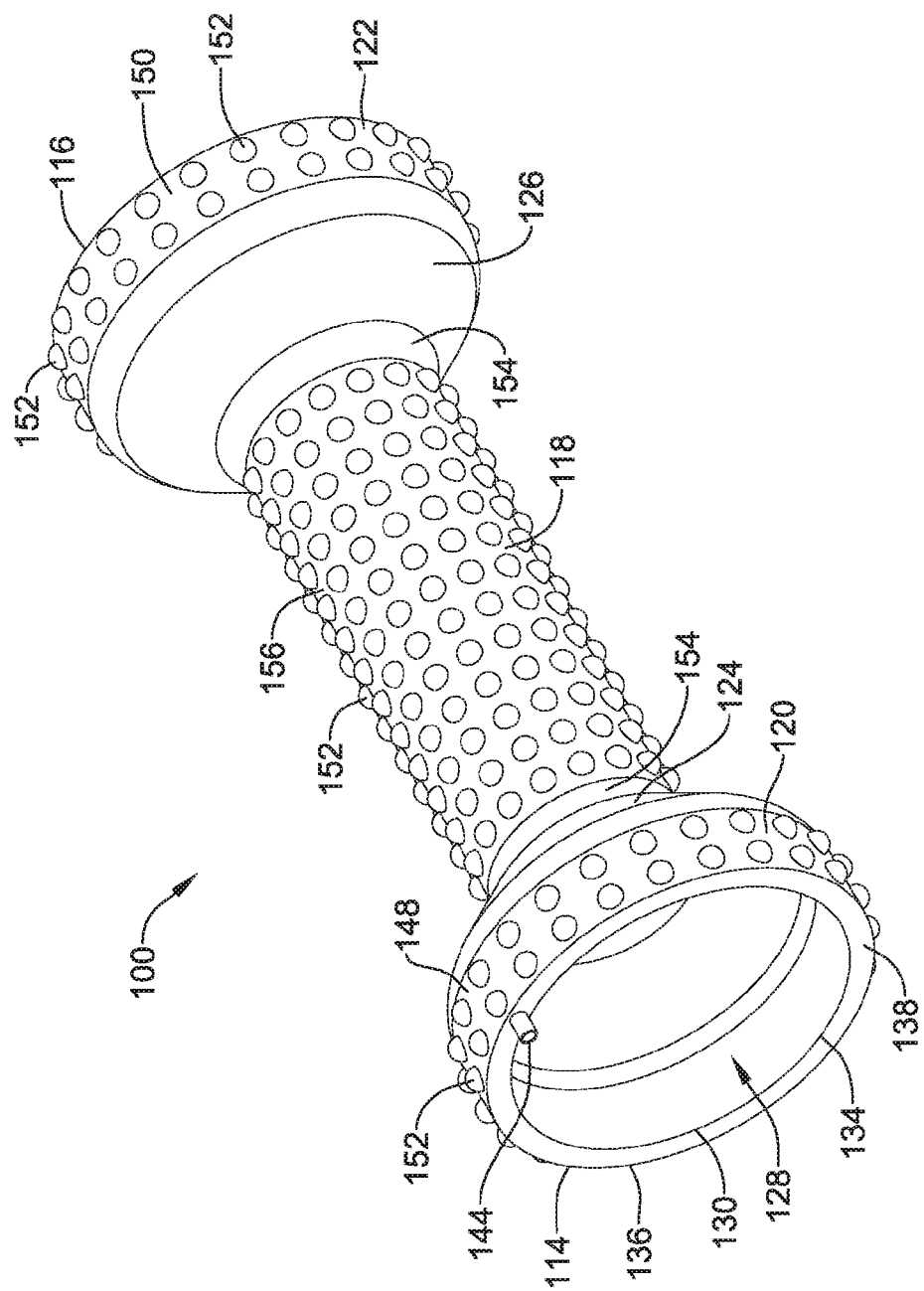
FIG. 5 a perspective view of another illustrative inflatable stent.

FIG. 5 illustrates a perspective view of another illustrative endoluminal implant 100, such as, but not limited to, a stent, which may be similar in form and function the stent 10 described above. In some instances, the stent 100 may be formed from an elongated tubular balloon having a first end 114, a second end 116, and an intermediate region 118 disposed between the first end 114 and the second end 116. The stent 100 may be expandable from a first collapsed configuration (not shown) to a second expanded configuration. The stent 100 may be structured to extend across a stricture in the esophagus to allow for the passage of foods, fluids, etc. In some instances, in the expanded configuration, the stent 100 may include a first end region 120 and a second end region 122. In some embodiments, the first end region 120 and the second end region 122 may include retention features or anti-migration flares 148, 150 positioned adjacent to the first end 114 and the second end 116 of the stent 100. The anti-migration flares 148, 150 may be configured to engage an interior portion the walls of the esophagus. In some embodiments, the retention features 148, 150 may have a larger diameter than an intermediate portion 118 of the stent 100 to prevent the stent 100 from migrating once placed in the esophagus. It is contemplated that the transition 124, 126 from the cross-sectional area of the intermediate region 118 to the retention features 148, 150 may be gradual, sloped, or occur in an abrupt step-wise manner, as desired.

In some embodiments, the first anti-migration flare 148 may have a first outer diameter and the second anti-migration flare 150 may have a second outer diameter. In some instances, the first and second outer diameters may be approximately the same, while in other instances, the first and second outer diameters may be different. In some embodiments, the stent 100 may include only one or none of the anti-migration flares 148, 150. For example, the first end region 120 may include an anti-migration flare 148 while the second end region 122 may have an outer diameter similar to the intermediate region 118. It is further contemplated that the second end region 122 may include an anti-migration flare 150 while the first end region 120 may have an outer diameter similar to an outer diameter of the intermediate region 118. These are just examples. In some embodiments, the stent 100 may have a uniform outer diameter from the first end 114 to the second end 116.

In addition to, or in place of, anti-migration flares 148, 150, the outer surface of the stent 100 may include a textured surface 156 to help prevent migration of the stent 100. In some embodiments, the textured surface 156 may extend over the entire length and/or circumference of the stent 100. In other embodiments, the textured surface 156 may extend over only a portion of the length and/or circumference of the stent 100. The textured surface 156 may include a series of bumps or projections 152 disposed along the outer surface of the stent 100. The textured surface 156 can be formed or defined in any suitable manner. For example, the textured surface 156 can be formed by scoring, grinding, scuffing, or otherwise altering the outer surface of the stent 100. The pattern of textured surface 156 may also vary and can be random, regular, intermittent, or any other suitable pattern.

Similarly, bumps 152 may be formed, defined, or attached to the stent 100 in any suitable manner. For example, bumps 152 (and/or textured surface 156) may be defined by grinding the stent 100. Alternatively, bumps 152 may be molded, bonded, or otherwise attached to the stent 100 in any suitable way. The pattern may also be random, regular, or intermittent. For example, bumps 152 may be disposed along only a portion of the surface area of the stent 100 or the entire surface area, as desired. The bumps 152 may have any suitable shape. For example, bumps may be rounded or cylindrical, squared, triangular or pyramidal, polygonal, pointed, blunted, and the like, or any other suitable shape.

The stent 100 may be formed from an elongated tubular inflatable balloon. While the stent 100 is described as generally tubular, it is contemplated that the stent 100 may take any cross-sectional shape desired. In some embodiments, the stent 100 may be formed from a high pressure material, such as, but not limited to, polyethylene terephthalate (PET), nylon, polyethylene (PE), polyurethane, or flexible polyvinyl chloride (PVC). In other embodiments, the stent 100 may be formed from a compliant, low pressure material, such as, but not limited to, silicone, synthetic polyisoprene, or latex. The stent 100 may include a lumen 128 extending from a first opening 130 adjacent the first end 114 to a second opening (not explicitly shown) adjacent to the second end 116 to allow for the passage of food, fluids, etc. The stent 100 may include an inner wall 134 and an outer wall 136. The inner wall 134 and the outer wall 136 may be connected by one or more side walls 138 adjacent the first and second ends 114, 116 to define an enclosed inflation chamber (not explicitly shown) extending from the first end 114 to the second end 116. In other embodiments, the inner wall 134 and the outer wall 136 may be secured directly to one another without the use of side walls 138. The inflation chamber may receive an inflation fluid through an inflation port or valve 144 to expand the stent 100 from a generally collapsed delivery configuration (not shown) to an expanded or deployed configuration, as shown in FIG. 5. The inflation fluid may be saline, a biocompatible liquid polymer, such as ENTERYX®, air, or other suitable inflation fluid. The inflation chamber may be similar in form and function to the inflation chamber 42 described above.

An inflation port or valve 144 may be positioned adjacent to the first end 114. However, in some instances, the inflation valve 144 may be positioned adjacent to the second end 116 or in the intermediate region 118, as desired. The inflation valve 144 may be in fluid communication with the inflation chamber to provide a regulated passage for an inflation fluid to travel into the inflation chamber of the stent 100. The inflation valve 144 may be any of a number of widely applied valves, applicable in surgeries and medical implants, and may be made from a biocompatible material. In some embodiments, the inflation valve 144 may be a unidirectional valve that provides a regulated passage for an amount of a suitable fluid into the inflation chamber of the inflatable stent 100. For example, the inflation valve 144 may provide such a passage upon an application of pressure from a catheter lumen or an inflation device that is introduced into the stent 100 for the balloon's inflation. Once the application of pressure is removed, a diaphragm or other sealing mechanism may seal the inflation chamber to maintain the stent 100 in the inflated state.

In some embodiments, the inflation valve 144 may comprise a break away port. The valve 144 may be affixed to a delivery device during delivery and inflation of the stent 100 and break away from the delivery device once the stent 100 has been inflated to a desired pressure. While the inflation valve 144 is illustrated as extending from the first end 114 of the stent 100, it is contemplated that the inflation valve 144 may be positioned at other locations along the stent 100, as desired. For example, in some instances, the inflation valve 144 may be incorporated into the inflation chamber such that it does not extend beyond the first end 114. In other instances, the inflation valve 144 may be disposed adjacent the second end 116. It is further contemplated that the inflation valve 144 may be positioned with the lumen 128 of the stent 100. For example, the inflation valve 144 may be positioned adjacent to the intermediate region 118 and accessible through the lumen 128 of the stent 100.

The stent 100 may further include one or more radiopaque marker elements 154. The marker elements 154 may be doped with, made of, or otherwise include a radiopaque material. Radiopaque materials are understood to be materials capable of producing a relatively bright image on a fluoroscopy screen or another imaging technique during a medical procedure. The marker elements 154 may be positioned at any location along the length of the stent 100 desired. In some instances, the marker elements 154 may be positioned adjacent to one or both of the first or second end regions 120, 122 to facilitate positioning of the anti-migration flares 148, 150. This is just an example.

Figure 6:
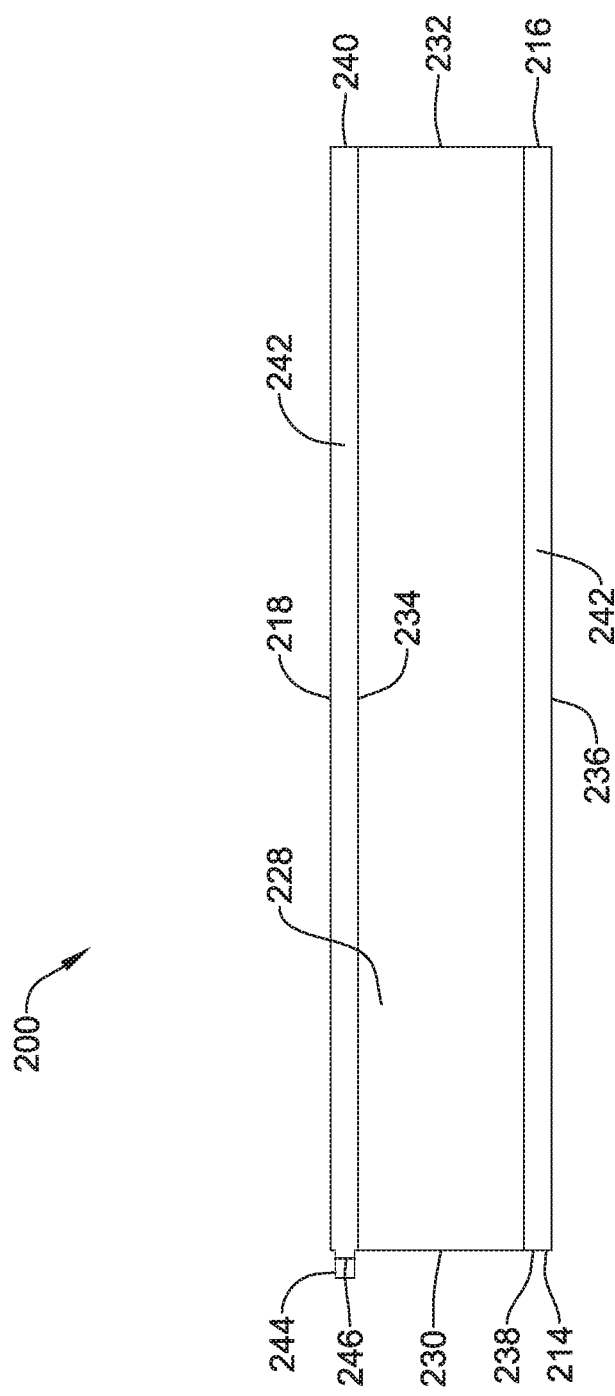
FIG. 6 is a cross-sectional view of another illustrative inflatable stent.

FIG. 6 illustrates a cross-sectional view of another illustrative endoluminal implant 200, such as, but not limited to, a stent, which may be similar in form and function the stent 10 described above. In some instances, the stent 200 may be formed from an elongated tubular balloon having a first end 214, a second end 216, and an intermediate region 218 disposed between the first end 214 and the second end 216. The stent 200 may be expandable from a first collapsed configuration (not shown) to a second expanded configuration. The stent 200 may be structured to extend across a stricture in the esophagus to allow for the passage of foods, fluids, etc. In some embodiments, the stent 200 may have a uniform outer diameter from the first end 214 to the second end 216, although this is not required.

While not explicitly shown, the outer surface of the stent 200 may include a textured surface to help prevent migration of the stent 200. In some embodiments, the textured surface may extend over the entire length and/or circumference of the stent 200. In other embodiments, the textured surface may extend over only a portion of the length and/or circumference of the stent 200. The textured surface may include a series of bumps, protrusions, recesses, cavities, grooves, etc. disposed along the outer surface of the stent 200. The textured surface can be formed or defined in any suitable manner. For example, the textured surface can be formed by scoring, grinding, scuffing, or otherwise altering the outer surface of the stent 200. The pattern of textured surface may also vary and can be random, regular, intermittent, or any other suitable pattern.

The stent 200 may be formed from an elongated tubular inflatable balloon. While the stent 200 is described as generally tubular, it is contemplated that the stent 200 may take any cross-sectional shape desired. In some embodiments, the stent 200 may be formed from a high pressure material, such as, but not limited to, polyethylene terephthalate (PET), nylon, polyethylene (PE), polyurethane, or flexible polyvinyl chloride (PVC). In other embodiments, the stent 200 may be formed from a compliant, low pressure material, such as, but not limited to, silicone, synthetic polyisoprene, or latex. The stent 200 may include a lumen 228 extending from a first opening 230 adjacent the first end 214 to a second opening 232 adjacent to the second end 216 to allow for the passage of food, fluids, etc. The stent 200 may include an inner wall 234 and an outer wall 236. The inner wall 234 and the outer wall 236 may be connected by one or more side walls 238, 240 adjacent the first and second ends 214, 216 to define an enclosed inflation chamber 242 extending from the first end 214 to the second end 216. In other embodiments, the inner wall 234 and the outer wall 236 may be secured directly to one another without the use of side walls 238, 240. The inflation chamber 242 may receive an inflation fluid through an inflation port or valve 244 to expand the stent 200 from a generally collapsed delivery configuration (not shown) to an expanded or deployed configuration, as shown in FIG. 6. The inflation fluid may be saline, a biocompatible liquid polymer, such as ENTERYX®, air, or other suitable inflation fluid. The inflation chamber 242 may be similar in form and function to the inflation chamber 42 described above.

An inflation port or valve 244 may be positioned adjacent to the first end 214. However, in some instances, the inflation valve 244 may be positioned adjacent to the second end 216 or in the intermediate region 218, as desired. The inflation valve 244 may be in fluid communication with the inflation chamber 242 to provide a regulated passage for an inflation fluid to travel into the inflation chamber of the stent 200. The inflation valve 244 may be any of a number of widely applied valves, applicable in surgeries and medical implants, and may be made from a biocompatible material. In some embodiments, the inflation valve 244 may be a unidirectional valve that provides a regulated passage for an amount of a suitable fluid into the inflation chamber of the inflatable stent 200. For example, the inflation valve 244 may provide such a passage upon an application of pressure from a catheter lumen or an inflation device that is introduced into the stent 200 for the balloon's inflation. Once the application of pressure is removed, a diaphragm or other sealing mechanism 246 may seal the inflation chamber 242 to maintain the stent 200 in the inflated state.

In some embodiments, the inflation valve 244 may comprise a break away port. The valve 244 may be affixed to a delivery device during delivery and inflation of the stent 200 and break away from the delivery device once the stent 200 has been inflated to a desired pressure. While the inflation valve 244 is illustrated as extending from the first end 214 of the stent 200, it is contemplated that the inflation valve 244 may be positioned at other locations along the stent 200, as desired. For example, in some instances, the inflation valve 244 may be incorporated into the inflation chamber such that it does not extend beyond the first end 214. In other instances, the inflation valve 244 may be disposed adjacent the second end 216. It is further contemplated that the inflation valve 244 may be positioned with the lumen 228 of the stent 200. For example, the inflation valve 244 may be positioned adjacent to the intermediate region 218 and accessible through the lumen 228 of the stent 200.

The stent 200 may further include one or more radiopaque marker elements (not explicitly shown). The marker elements may be doped with, made of, or otherwise include a radiopaque material. Radiopaque materials are understood to be materials capable of producing a relatively bright image on a fluoroscopy screen or another imaging technique during a medical procedure. The marker elements may be positioned at any location along the length of the stent 200 desired.

Figure 7:
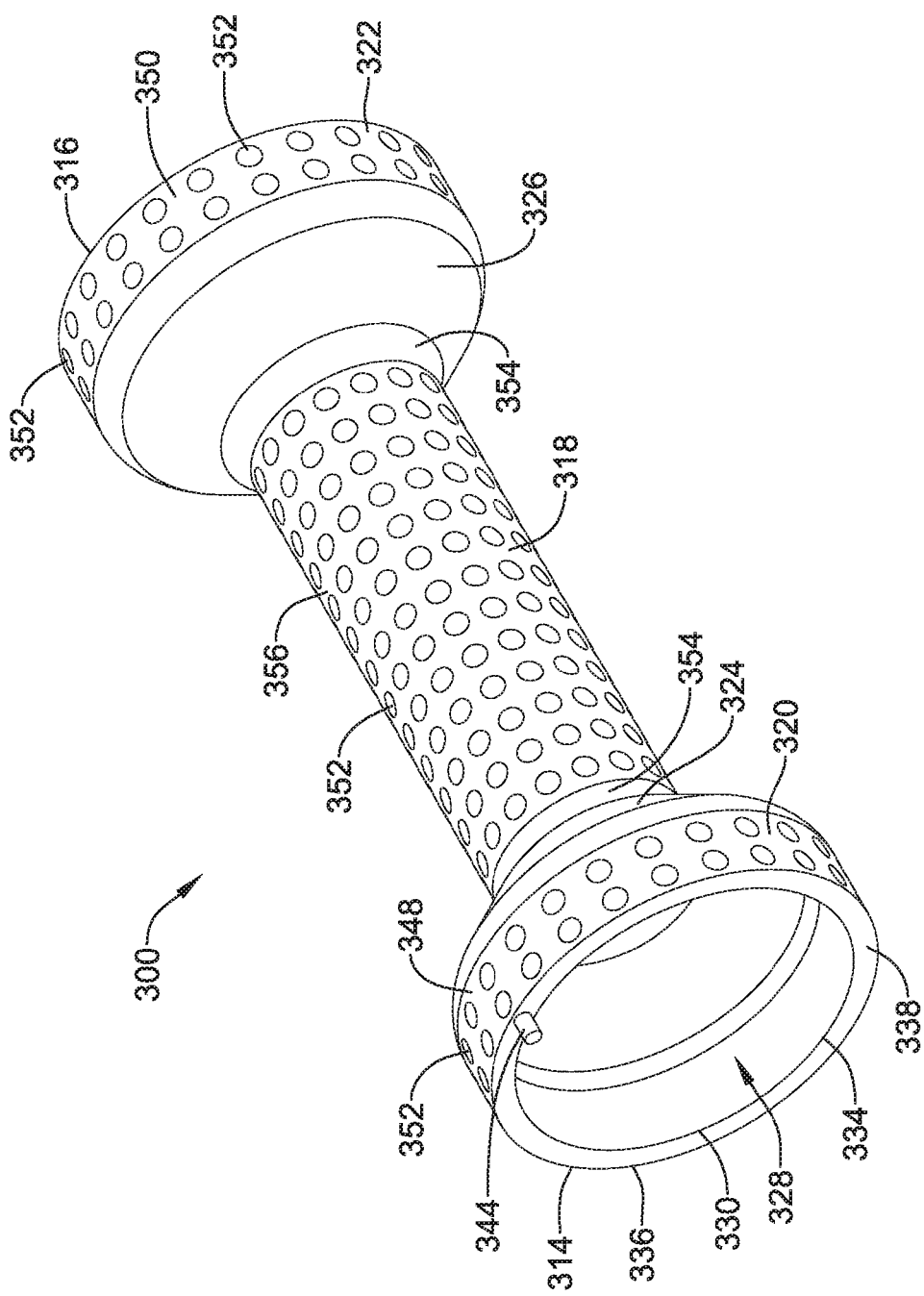
FIG. 7 is a perspective view of another illustrative inflatable stent.

FIG. 7 illustrates a perspective view of another illustrative endoluminal implant 300, such as, but not limited to, a stent, which may be similar in form and function the stent 10 described above. In some instances, the stent 300 may be formed from an elongated tubular balloon having a first end 314, a second end 316, and an intermediate region 318 disposed between the first end 314 and the second end 316. The stent 300 may be expandable from a first collapsed configuration (not shown) to a second expanded configuration. The stent 300 may be structured to extend across a stricture in the esophagus to allow for the passage of foods, fluids, etc. In some instances, in the expanded configuration, the stent 300 may include a first end region 320 and a second end region 322. In some embodiments, the first end region 320 and the second end region 322 may include retention features or anti-migration flares 348, 350 positioned adjacent to the first end 314 and the second end 316 of the stent 300. The anti-migration flares 348, 350 may be configured to engage an interior portion the walls of the esophagus. In some embodiments, the retention features 348, 350 may have a larger diameter than an intermediate portion 318 of the stent 300 to prevent the stent 300 from migrating once placed in the esophagus. It is contemplated that the transition 324, 326 from the cross-sectional area of the intermediate region 318 to the retention features 348, 350 may be gradual, sloped, or occur in an abrupt step-wise manner, as desired.

In some embodiments, the first anti-migration flare 348 may have a first outer diameter and the second anti-migration flare 350 may have a second outer diameter. In some instances, the first and second outer diameters may be approximately the same, while in other instances, the first and second outer diameters may be different. In some embodiments, the stent 300 may include only one or none of the anti-migration flares 348, 350. For example, the first end region 320 may include an anti-migration flare 348 while the second end region 322 may have an outer diameter similar to the intermediate region 318. It is further contemplated that the second end region 322 may include an anti-migration flare 350 while the first end region 320 may have an outer diameter similar to an outer diameter of the intermediate region 318. These are just examples. In some embodiments, the stent 300 may have a uniform outer diameter from the first end 314 to the second end 316.

In addition to, or in place of, anti-migration flares 348, 350, the outer surface of the stent 300 may include a textured surface 356 to help prevent migration of the stent 300. In some embodiments, the textured surface 356 may extend over the entire length and/or circumference of the stent 300. In other embodiments, the textured surface 356 may extend over only a portion of the length and/or circumference of the stent 300. The textured surface 356 may include a series of recesses, grooves, cavities, dimples, etc. 352 disposed along the outer surface of the stent 300. The textured surface 356 can be formed or defined in any suitable manner. For example, the textured surface 356 can be formed by scoring, grinding, scuffing, or otherwise altering the outer surface of the stent 300. The pattern of textured surface 356 may also vary and can be random, regular, intermittent, or any other suitable pattern.

Similarly, recesses 352 may be formed or defined within the stent 300 in any suitable manner. For example, recesses 352 (and/or textured surface 356) may be defined by grinding the stent 300. Alternatively, recesses 352 may be molded into the stent 300 in any suitable way. The pattern may also be random, regular, or intermittent. For example, recesses 352 may be disposed along only a portion of the surface area of the stent 300 or the entire surface area, as desired. The recesses 352 may have any suitable shape. For example, recesses may be rounded or cylindrical, squared, triangular or pyramidal, polygonal, pointed, blunted, and the like, or any other suitable shape.

The stent 300 may be formed from an elongated tubular inflatable balloon. While the stent 300 is described as generally tubular, it is contemplated that the stent 300 may take any cross-sectional shape desired. In some embodiments, the stent 300 may be formed from a high pressure material, such as, but not limited to, polyethylene terephthalate (PET), nylon, polyethylene (PE), polyurethane, or flexible polyvinyl chloride (PVC). In other embodiments, the stent 300 may be formed from a compliant, low pressure material, such as, but not limited to, silicone, synthetic polyisoprene, or latex. The stent 300 may include a lumen 328 extending from a first opening 330 adjacent the first end 314 to a second opening (not explicitly shown) adjacent to the second end 316 to allow for the passage of food, fluids, etc. The stent 300 may include an inner wall 334 and an outer wall 336. The inner wall 334 and the outer wall 336 may be connected by one or more side walls 338 adjacent the first and second ends 314, 316 to define an enclosed inflation chamber (not explicitly shown) extending from the first end 314 to the second end 316. In other embodiments, the inner wall 334 and the outer wall 336 may be secured directly to one another without the use of side walls 338. The inflation chamber may receive an inflation fluid through an inflation port or valve 344 to expand the stent 300 from a generally collapsed delivery configuration (not shown) to an expanded or deployed configuration, as shown in FIG. 7. The inflation fluid may be saline, a biocompatible liquid polymer, such as ENTERYX®, air, or other suitable inflation fluid. The inflation chamber may be similar in form and function to the inflation chamber 42 described above.

An inflation port or valve 344 may be positioned adjacent to the first end 314. However, in some instances, the inflation valve 344 may be positioned adjacent to the second end 316 or in the intermediate region 318, as desired. The inflation valve 344 may be in fluid communication with the inflation chamber to provide a regulated passage for an inflation fluid to travel into the inflation chamber of the stent 300. The inflation valve 344 may be any of a number of widely applied valves, applicable in surgeries and medical implants, and may be made from a biocompatible material. In some embodiments, the inflation valve 344 may be a unidirectional valve that provides a regulated passage for an amount of a suitable fluid into the inflation chamber of the inflatable stent 300. For example, the inflation valve 344 may provide such a passage upon an application of pressure from a catheter lumen or an inflation device that is introduced into the stent 300 for the balloon's inflation. Once the application of pressure is removed, a diaphragm or other sealing mechanism may seal the inflation chamber to maintain the stent 300 in the inflated state.

In some embodiments, the inflation valve 344 may comprise a break away port. The valve 344 may be affixed to a delivery device during delivery and inflation of the stent 300 and break away from the delivery device once the stent 300 has been inflated to a desired pressure. While the inflation valve 344 is illustrated as extending from the first end 314 of the stent 300, it is contemplated that the inflation valve 344 may be positioned at other locations along the stent 300, as desired. For example, in some instances, the inflation valve 344 may be incorporated into the inflation chamber such that it does not extend beyond the first end 314. In other instances, the inflation valve 344 may be disposed adjacent the second end 316. It is further contemplated that the inflation valve 344 may be positioned with the lumen 328 of the stent 300. For example, the inflation valve 344 may be positioned adjacent to the intermediate region 318 and accessible through the lumen 328 of the stent 300.

The stent 300 may further include one or more radiopaque marker elements 354. The marker elements 354 may be doped with, made of, or otherwise include a radiopaque material. Radiopaque materials are understood to be materials capable of producing a relatively bright image on a fluoroscopy screen or another imaging technique during a medical procedure. The marker elements 354 may be positioned at any location along the length of the stent 300 desired. In some instances, the marker elements 354 may be positioned adjacent to one or both of the first or second end regions 320, 322 to facilitate positioning of the anti-migration flares 348, 350. This is just an example.

Figure 8:
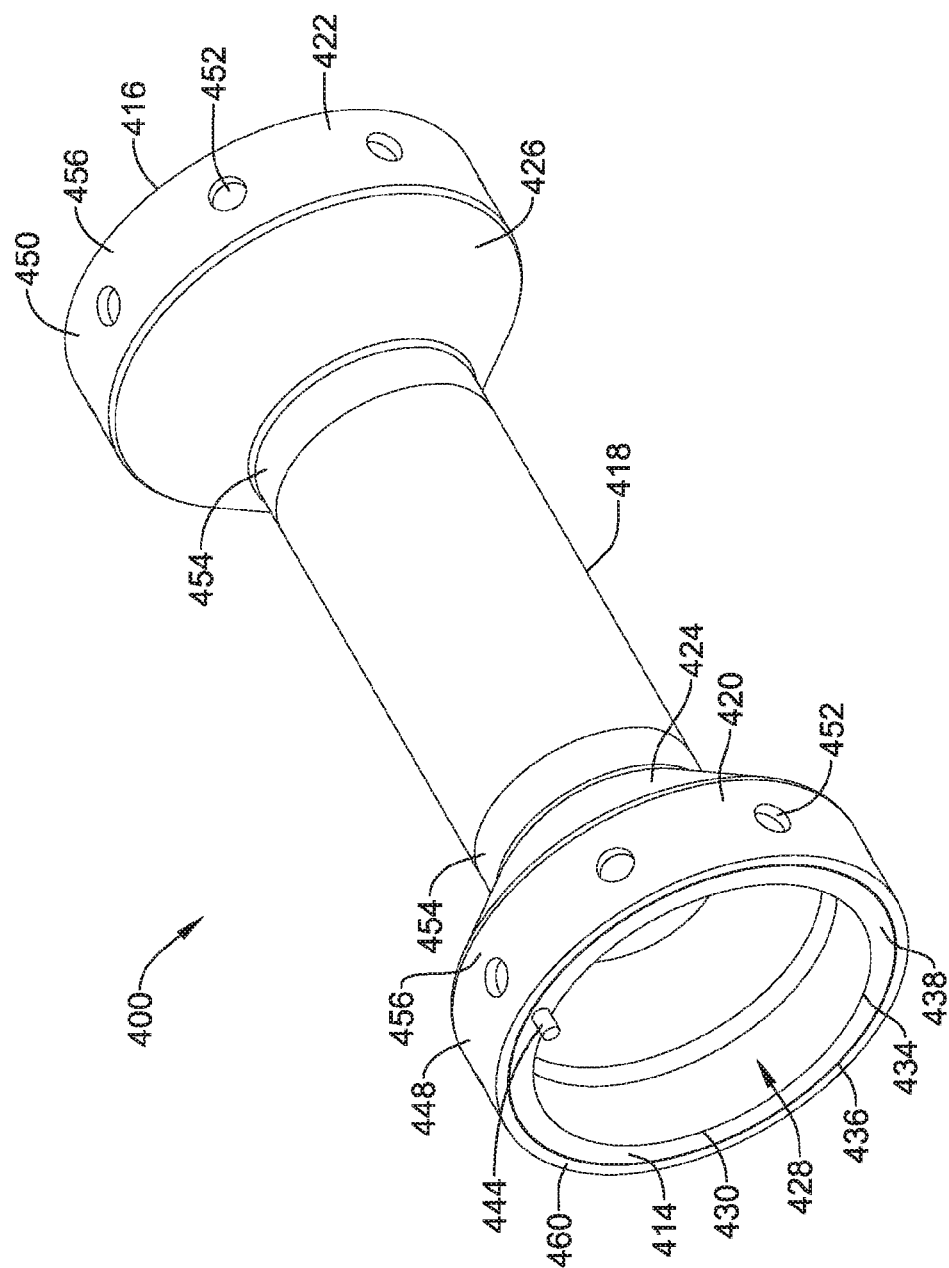
FIG. 8 is a perspective view of another illustrative inflatable stent.

FIG. 8 illustrates a perspective view of another illustrative endoluminal implant 400, such as, but not limited to, a stent, which may be similar in form and function the stent 10 described above. In some instances, the stent 400 may be formed from an elongated tubular balloon having a first end 414, a second end 416, and an intermediate region 418 disposed between the first end 414 and the second end 416. The stent 400 may be expandable from a first collapsed configuration (not shown) to a second expanded configuration. The stent 400 may be structured to extend across a stricture in the esophagus to allow for the passage of foods, fluids, etc. In some instances, in the expanded configuration, the stent 400 may include a first end region 420 and a second end region 422. In some embodiments, the first end region 420 and the second end region 422 may include retention features or anti-migration flares 448, 450 positioned adjacent to the first end 414 and the second end 416 of the stent 400. The anti-migration flares 448, 450 may be configured to engage an interior portion the walls of the esophagus. In some embodiments, the retention features 448, 450 may have a larger diameter than an intermediate portion 418 of the stent 400 to prevent the stent 400 from migrating once placed in the esophagus. It is contemplated that the transition 424, 426 from the cross-sectional area of the intermediate region 418 to the retention features 448, 450 may be gradual, sloped, or occur in an abrupt step-wise manner, as desired.

In some embodiments, the first anti-migration flare 448 may have a first outer diameter and the second anti-migration flare 450 may have a second outer diameter. In some instances, the first and second outer diameters may be approximately the same, while in other instances, the first and second outer diameters may be different. In some embodiments, the stent 400 may include only one or none of the anti-migration flares 448, 450. For example, the first end region 420 may include an anti-migration flare 448 while the second end region 422 may have an outer diameter similar to the intermediate region 418. It is further contemplated that the second end region 422 may include an anti-migration flare 450 while the first end region 420 may have an outer diameter similar to an outer diameter of the intermediate region 418. These are just examples. In some embodiments, the stent 400 may have a uniform outer diameter from the first end 414 to the second end 416.

In addition to, or in place of, anti-migration flares 448, 450, the outer surface of the stent 400 may include a textured surface 456 to help prevent migration of the stent 400. In some embodiments, the textured surface 456 may extend over the entire length and/or circumference of the stent 400. In other embodiments, the textured surface 456 may extend over only a portion of the length and/or circumference of the stent 400. The textured surface 456 may include a series of recesses, grooves, cavities, through holes, etc. 452 disposed along the outer surface of the stent 400. In some embodiments, the stent 400 may be provided with an additional layer of material, or an outer layer 460 disposed over an outer wall 436 of an inflatable portion of the stent 400. This may allow through holes 452 to extend from an outer surface of the outer layer 460 to an inner surface of the outer layer 460, if desired, while still allowing for inflation of the stent 400. The through holes 452 may allow for tissue ingrowth into the stent 400 to further secure the stent. The textured surface 456 can be formed or defined in any suitable manner. For example, the textured surface 456 can be formed by scoring, grinding, scuffing, or otherwise altering the outer surface of the stent 400. The pattern of textured surface 456 may also vary and can be random, regular, intermittent, or any other suitable pattern.

Similarly, the through holes 452 may be formed or defined within the outer layer 460 in any suitable manner. For example, through holes 452 (and/or textured surface 456) may be defined by grinding or drilling into the stent 400. Alternatively, the through holes 452 may be molded into the stent 400 in any suitable way. The pattern may also be random, regular, or intermittent. For example, the through holes 452 may be disposed along only a portion of the surface area of the stent 400 or the entire surface area, as desired. The through holes 452 may have any suitable shape. For example, the through holes 452 may be rounded or cylindrical, squared, triangular or pyramidal, polygonal, pointed, blunted, and the like, or any other suitable shape.

The stent 400 may be formed from an elongated tubular inflatable balloon. While the stent 400 is described as generally tubular, it is contemplated that the stent 400 may take any cross-sectional shape desired. In some embodiments, the stent 400 may be formed from a high pressure material, such as, but not limited to, polyethylene terephthalate (PET), nylon, polyethylene (PE), polyurethane, or flexible polyvinyl chloride (PVC). In other embodiments, the stent 400 may be formed from a compliant, low pressure material, such as, but not limited to, silicone, synthetic polyisoprene, or latex. The stent 400 may include a lumen 428 extending from a first opening 430 adjacent the first end 414 to a second opening (not explicitly shown) adjacent to the second end 416 to allow for the passage of food, fluids, etc. An inflatable portion of the stent 400 may include an inner wall 434 and an outer wall 436. The inner wall 434 and the outer wall 436 may be connected by one or more side walls 438 adjacent the first and second ends 414, 416 to define an enclosed inflation chamber (not explicitly shown) extending from the first end 414 to the second end 416. In other embodiments, the inner wall 434 and the outer wall 436 may be secured directly to one another without the use of side walls 438. The inflation chamber may receive an inflation fluid through an inflation port or valve 444 to expand the stent 400 from a generally collapsed delivery configuration (not shown) to an expanded or deployed configuration, as shown in FIG. 8. The inflation fluid may be saline, a biocompatible liquid polymer, such as ENTERYX®, air, or other suitable inflation fluid. The inflation chamber may be similar in form and function to the inflation chamber 42 described above.

An inflation port or valve 444 may be positioned adjacent to the first end 414. However, in some instances, the inflation valve 444 may be positioned adjacent to the second end 416 or in the intermediate region 418, as desired. The inflation valve 444 may be in fluid communication with the inflation chamber to provide a regulated passage for an inflation fluid to travel into the inflation chamber of the stent 400. The inflation valve 444 may be any of a number of widely applied valves, applicable in surgeries and medical implants, and may be made from a biocompatible material. In some embodiments, the inflation valve 444 may be a unidirectional valve that provides a regulated passage for an amount of a suitable fluid into the inflation chamber of the inflatable stent 400. For example, the inflation valve 444 may provide such a passage upon an application of pressure from a catheter lumen or an inflation device that is introduced into the stent 400 for the balloon's inflation. Once the application of pressure is removed, a diaphragm or other sealing mechanism may seal the inflation chamber to maintain the stent 400 in the inflated state.

In some embodiments, the inflation valve 444 may comprise a break away port. The valve 444 may be affixed to a delivery device during delivery and inflation of the stent 400 and break away from the delivery device once the stent 400 has been inflated to a desired pressure. While the inflation valve 444 is illustrated as extending from the first end 414 of the stent 400, it is contemplated that the inflation valve 444 may be positioned at other locations along the stent 400, as desired. For example, in some instances, the inflation valve 444 may be incorporated into the inflation chamber such that it does not extend beyond the first end 414. In other instances, the inflation valve 444 may be disposed adjacent the second end 416. It is further contemplated that the inflation valve 444 may be positioned with the lumen 428 of the stent 400. For example, the inflation valve 444 may be positioned adjacent to the intermediate region 418 and accessible through the lumen 428 of the stent 400.

The stent 400 may further include one or more radiopaque marker elements 454. The marker elements 454 may be doped with, made of, or otherwise include a radiopaque material. Radiopaque materials are understood to be materials capable of producing a relatively bright image on a fluoroscopy screen or another imaging technique during a medical procedure. The marker elements 454 may be positioned at any location along the length of the stent 400 desired. In some instances, the marker elements 454 may be positioned adjacent to one or both of the first or second end regions 420, 422 to facilitate positioning of the anti-migration flares 448, 450. This is just an example.

The stents, delivery systems, and the various components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. In some other embodiments, a superelastic alloy, for example a superelastic nitinol can be used to achieve desired properties.

In at least some embodiments, portions or all of the stents or delivery systems may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of the stents or delivery systems in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents or delivery systems to achieve the same result.

In some embodiments, a degree of Magnetic Resonance Imaging (MM) compatibility is imparted into the stents or delivery systems. For example, the stents or delivery systems or portions thereof, may be made of a material that does not substantially distort the image and create substantial artifacts (i.e., gaps in the image). Certain ferromagnetic materials, for example, may not be suitable because they may create artifacts in an MRI image. The stents or delivery systems or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for the stents or delivery systems may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent, the stent comprising:
    an elongated tubular balloon having a first end and a second end and an intermediate region disposed therebetween, the elongated tubular balloon having a lumen extending from the first end to the second end;
    an inflation chamber extending continuously from the first end to the second end of the elongated tubular balloon, the inflation chamber including a first flared portion at the first end, a second flared portion at the second end, and a body portion therebetween, wherein the body portion of the inflation chamber is defined between a radially outward wall and a radially inward wall of the inflation chamber, the radially inward wall defining the lumen of the elongated tubular balloon through a length of the elongated tubular balloon;
    an outer layer disposed over at least a portion of an outer surface of the outer wall;
    a plurality of holes positioned adjacent to the first and/or second ends of the elongated tubular balloon and extending from an outer surface of the outer layer to the outer surface of the outer wall, the plurality of holes configured to contact a body lumen when the elongated tubular balloon is in an expanded configuration; and
    an inflation valve.

2. The stent of claim 1, wherein the inflation valve is disposed adjacent to one of the first or second ends of the elongated tubular balloon.

3. The stent of claim 1, wherein the first end has an outer diameter larger than an outer diameter of the intermediate region and the second end has an outer diameter larger than an outer diameter of the intermediate region.

4. The stent of claim 1, wherein the inflation valve comprises a one-way valve.

5. The stent of claim 1 wherein an outer surface of the outer wall comprises a textured surface.

6. The stent of claim 1, wherein the elongated tubular balloon comprises polyethylene terephthalate.

7. The stent of claim 1, further comprising at least one radiopaque marker element.

8. A stent, the stent comprising:
    an elongated tubular balloon, the elongated tubular balloon comprising:
        a flared first end and a flared second end and an intermediate region disposed therebetween;
        a radially inward wall and a radially outward wall, the radially inward wall and the radially outward wall connected at both the flared first end and the flared second end to define an enclosed inflation chamber between the radially inward wall and the radially outward wall;
    an outer layer disposed over at least a portion of an outer surface of the outer wall;
    a plurality of holes positioned adjacent to the flared first end and/or the flared second end and extending from an outer surface of the outer layer to the outer surface of the outer wall, the plurality of holes configured to contact a body lumen when the elongated tubular balloon is in an expanded configuration to allow for tissue ingrowth;
    wherein an inner surface of the radially inward wall of the elongated tubular balloon defines a lumen extending from the first end to the second end of the elongated tubular balloon; and
    an inflation valve disposed adjacent to the first end of the elongated tubular balloon.

9. The stent of claim 8, wherein the flared first end has an outer diameter larger than an outer diameter of the intermediate region.

10. The stent of claim 8, wherein the flared second end has an outer diameter larger than an outer diameter of the intermediate region.

11. The stent of claim 8, wherein the inflation valve comprises a one-way valve.

12. The stent of claim 8, wherein a portion of an outer surface of the radially outward wall comprises a textured surface.

13. The stent of claim 8, wherein the elongated tubular balloon comprises polyethylene terephthalate.

14. The stent of claim 8, further comprising at least one radiopaque marker element.

15. A stent, the stent comprising:
    an elongated tubular balloon, the elongated tubular balloon comprising:
        a flared proximal end having a first outer diameter and a flared distal end having a second outer diameter and an intermediate region having a third outer diameter smaller than both the first outer diameter and the second outer diameter disposed between the flared proximal end and the flared distal end, the flared first end and/or the flared second end including a plurality of through holes, the plurality of through holes configured to contact a body lumen when the elongated tubular balloon is in an expanded configuration to allow for tissue ingrowth;
        an inner wall and an outer wall extending along a length of the elongated tubular balloon, the inner wall and the outer wall connected at both the proximal end and the distal end to define an enclosed inflation chamber between the inner wall and the outer wall;
        wherein an inner surface of the inner wall of the elongated tubular balloon defines a through lumen extending from the proximal end to the distal end of the elongated tubular balloon; and an inflation valve disposed adjacent to the proximal end of the elongated tubular balloon.

\* \* \* \* \*